US008541545B2

(12) United States Patent
Gruber

(10) Patent No.: US 8,541,545 B2
(45) Date of Patent: Sep. 24, 2013

(54) STABILIZED MELANOCORTIN LIGANDS

(75) Inventor: Kenneth A. Gruber, Columbia, MO (US)

(73) Assignee: Tensive Controls Inc., Columbia, MO (US)

( * ) Notice: Subject to any disclaimer, the term of this patent is extended or adjusted under 35 U.S.C. 154(b) by 0 days.

(21) Appl. No.: 13/389,820

(22) PCT Filed: Aug. 30, 2010

(86) PCT No.: PCT/US2010/047108
§ 371 (c)(1),
(2), (4) Date: Apr. 30, 2012

(87) PCT Pub. No.: WO2011/026015
PCT Pub. Date: Mar. 3, 2011

(65) Prior Publication Data
US 2012/0220525 A1    Aug. 30, 2012

Related U.S. Application Data

(60) Provisional application No. 61/238,625, filed on Aug. 31, 2009.

(51) Int. Cl.
| | | |
|---|---|---|
| A61K 38/00 | (2006.01) | |
| A61K 38/12 | (2006.01) | |
| C07K 2/00 | (2006.01) | |
| C07K 4/00 | (2006.01) | |
| C07K 5/00 | (2006.01) | |
| C07K 7/00 | (2006.01) | |
| C07K 14/00 | (2006.01) | |
| C07K 16/00 | (2006.01) | |
| C07K 17/00 | (2006.01) | |

(52) U.S. Cl.
USPC .......................................... 530/300; 530/317

(58) Field of Classification Search
None
See application file for complete search history.

(56) References Cited

U.S. PATENT DOCUMENTS

2005/0038230 A1 *  2/2005  Sharma et al. ............... 530/350

FOREIGN PATENT DOCUMENTS

WO    WO 2009061411 A2    5/2009

OTHER PUBLICATIONS

Gomes et al., Vaccine, 2000, 18, 362-370.*
Biochem Biophys. Res. Commun., 2001, 286(3):641-645.*
Mayorov et al., 2006, J Med Chem., 49:1946-1952.*
al-Obeidi et al., "Potent and Prolonged Acting Cyclic Lactam Analogues of a-Melanotropin: Design Based on Molecular Dynamics," *J. Med. Chem*, 32(12): 2555-2561 (1989).
Ballet, S., et al., "Novel selective human melanocortin-3 receptor ligands: Use of the 4-amino-1,2,4,5-tetrahydro-2-benzazepin-3-one (Aba) scaffold," *Bioorganic & Med. Chem. Lett.*,17:2492-2498 (2007).
Balse-Srinivasan et al., "Structure-Activity Relationships of Novel Cyclic r-MSH/â-MSH Hybrid Analogues That Lead to Potent and Selective Ligands for the Human MC3R and Human MC5R," *J. Med. Chem.*, 46(17):3728-3733 (2003).
Balse-Srinivasan. P., et al., "Structure-Activity Relationships of ç-MSH Analogues at the Human Melanocortin MC3, MC4, and MC5 Receptors. Discovery of Highly Selective hMC3R, hMC4R, and hMC5R Analogues," *J. Med. Chem*, 46:4965-4973 (2003).
Bazzani, C., et al., "Involvement of the central nervous system in the protective effect of melanocortins in myocardial ischaemia/reperfusion injury," *Resuscitation*, 52(1):109-115 (2002).
Bednarek et al., "Potent and Selective Peptide Agonists of a-Melanotropin Action at Human Melanocortin Receptor 4: Their Synthesis and Biological Evaluation in Vitrol," *Biochem Biophys. Res. Commun.*, 286(3):641-645 (2001).
Bednarek, M.A., "Potent and Selective Peptide Agonists of a-Melanocyte Stimulating Hormone (aMSH) Action at Human Melanocortin Receptor 5; their Synthesis and Biological Evaluation in vitro," *Chem. Biol. Drug Design*, 69:350-355 (2007).
Bednarek, M.A., et al., "Potent and Selective Agonists of Human Melanocortin Receptor 5: Cyclic Analogues of r-Melanocyte-Stimulating Hormone," *J. Med Chem.*, 50:2520-2526 (2007).
Bertonlini, A., et al., "Brain effects of melanocortins," *Pharmacol. Res*, 59(1):13-47 (2009).
Bhatt, U and Just, G, "Synthesis of a Novel Thyrotropin Releasing Hormone (TRH) Analog Incorporating a Piperazin-2-one Ring," *Helvetica Chimica Acta*, 83:722-727 (2000).
Cheung A.W.-H., et al., "Structure-Activity Relationship of Cyclic Peptide Penta-c[Asp-His6-DPhe7-Arg8-Trp9-Lys]-NH2 at the Human Melanocortin-1 and -4 Receptors: His6 Substitution," *Bioorganic & Med. Chem. Lett.*, 13:1307-1311 (2003).
Clements et al., "FMRFamide-Related Neuropeptides Are Agonists of the Orphan G-Protein-Coupled Receptor GPR54," *Biochem. Biophys. Res. Commun.*, 284:1189-1193 (2001).
Cone, R.D., "Anatomy and regulation of the central melanocortin system," *Nat. Neurosci*, 8(5):571-578 (2005).
Cone, R.D., "Studies on the Physiological Functions of the Melanocortin System," *Endocr. Rev.*, 27(7):736-749 (2006).
Greenfield et al., "Modulation of Blood Pressure by Central Melanocortinergic Pathways," *N. Eng. J. Med*. 360:44-52 (2009).
Grieco, P., et al., "Further structure-activity studies of lactam derivatives of MT-II and SHU-9119: Their activity and selectivity at human melanocortin receptors 3, 4, and 5," *Peptides* 28:1191-1196 (2007).

(Continued)

Primary Examiner — Marcela M Cordero Garcia
Assistant Examiner — Kaipeen Yang
(74) *Attorney, Agent, or Firm* — Womble Carlyle Sandridge & Rice, LLP

(57)    ABSTRACT

Compositions and methods are disclosed for a non-naturally occurring melanocortin ligand comprised of a melanocortin analog coupled to a degradation-resistant C-terminal extension and, optionally, an N-terminal extension, to produce a stable melanocortin ligand having diminished or abolished cardiovascular activity while retaining desired melanocortin regulatory activity.

11 Claims, No Drawings

(56) References Cited

OTHER PUBLICATIONS

Gruber, et al., "Natriuretic and Hypertensive Activities Reside in a Fragment of ACTH," *Hypertension*, 6:468-474 (1984).

Hess et al., "Effect of Structural and Conformation Modifications, Including Backbone Cyclization, of Hydrophilic Hexapeptides on Their Intestinal Permeability and Enzymatic Stability,"*J. Med. Chem.*, 50:6201-6211 (2007).

Holder, J. R. et al., "Structure-Activity Relationships of the Melanocortin Tetrapeptide Ac-His-DPhe-Arg-Trp-NH2 at the Mouse Melanocortin Receptors: Part 2 Modifications at the Phe Position," *J. Med. Chem.*, 45, 3073-3081 (2002).

Holder, J.R. and C. Haskel-Luevano, "Melanocortin Ligands: 30Years of Structure ⋀ Activity Relationship (SAR) Studies," *Med. Res. Rev.*, 24(3):325-356 (2004).

Holder, J.R. et al., "Structure-activity relationships of the melanocortin tetrapeptide Ac-His-DPhe-Arg-Trp-NH2 at the mouse melanocortin receptors Part 3: modifications at the Arg position," *Peptides*, 24:73-82 (2003).

Holder, J.R., et al., "Structure-Activity Relationships of the Melanocortin Tetrapeptide Ac-His-D-Phe-Arg-Trp-NH2 at the Mouse Melanocortin Receptors. 4. Modifications at the Trp Position," *J. Med. Chem.*, 45:5736-5744 (2002).

Hruby et al., "Cyclic Lactam a-Melanotropin balogues of Ac-Nle4-cyclo{Asp5,~Phe7,Lys10] a-Melanocyte-StimulatingH ormone-(4-10)-NH2 with Bulky Aromatic Amino Acids at Position 7 Show High Antagonist Potency and Selectivity at Specific Melanocortin Receptors," *J. Med. Chem.*, 38:3454-3461 (1995).

Jayawickreme et al., "Discovery and Structure-Function Analysios f a-Melanocyte-stimulating Hormone Antagonists," *J. Biol. Chem.*, 269:29846-29854 (1994).

Kavarana, et al., "Novel Cyclic Templates of r-MSH Give Highly Selective and Potent Antagonists/ Agonists for Human Melanocortin-¾ Receptors," *J. Med. Chem.*, 45(12):2644-2650 (2002).

Klein et al., "Pressor and Cardioaccelerator Effects of Gamma MSH and Related Peptides," *Life Sci*. 36:769-775 (1985).

Klemes et al. "Potenta Nd Prolongemde Lanotropiacc Tivities of the a-MSH Fragmenat Nalog, AC-[Nle4, I)-Phe']-o-MSH4-g-NH2," *Biochem. Biophys. Res. Commun.*, 137(2):722-728 (1986).

Masman et al., "Structure-antifungal activity relationship of His-Phe-Arg-Trp-Gly-Lys-Pro-Val-NH2 and analogues," *Bioorg. Med. Chem.*, 16(8):4347-58 (2008).

Mayorov et al., "Development of Cyclic ç-MSH Analogues with Selective hMC3R Agonist and hMC3R/hMC5R Antagonist Activities," *J. Med. Chem.*, 49:1946-1952 (2006).

Mayorov, A.V. et al., "Structure-Activity Relationships of Cyclic Lactam Analogues of r-Melanocyte-Stimulating Hormone (r-MSH) Targeting the Human Melanocortin-3 Receptor," *J. Med. Chem*. 51:187-195 (2008).

Mohamed, N., et al., "Efficient Synthesis of Substituted Oxopiperazines From Amino Acids," *Tetrahedron Lett.*, 39:8213-8216 (1998).

Nordheim et al., "Cardiovascular responses to melanocortin 4-receptor stimulation in conscious unrestrained normotensive rats," *Peptides* 27:438-443 (2006).

Stieber et al., "Bradycardic and Proarrhythmic Properties of Sinus Node Inhibitors," *Mol. Pharmacol.*, 69(4): 1328-37 (2006).

Strader, A.D., et al., "The Effects of the Melanocortin Agonist (MT-II) on Subcutaneous and Visceral Adipose Tissue in Rodents," *J. Pharmacol. Exp. Ther*., 322(3): 1153-1161 (2007).

Teixido, M., et al., "Exploratory neuropharmacological evaluation of a conformationally constrained thyrotropin-releasing hormone analogue," *Brain Res. Bull.*, 73(1-3):103-107 (2007).

Tugyi et al., "Partial D-amino acid substitution: Improved enzymatic stability and preserved Ab recognition of a MUC2 epitope peptide," *Proc. Nat. Acad. Sci*. (USA), 102(2):413-418 (2005).

Vig, B.S., et al., "Synthesis and Opioid Activity of Side-Chain-to-Side-Chain Cyclic Dynorphin A-(1-11) Amide Analogues Cyclized between Positions 2 and 5. 1. Substitutions in Position 3," *J. Med. Chem.*, 47(2):446-455 (2004).

Fields, G.B. and R.L. Noble, "Solid phase peptide synthesis utilizing 9-fluorenylmethoxycarbonyl amino acids," *Intl. J. Peptide Protein Res*. 35:161-214 (1990).

Gruber, K.A. and M.F. Callahan, "ACTH-(4-10) Through y-MSH: Evidence for a New Class of Central Autonomic Nervous system-regulating peptides," *Am. J. Physiol.*, 257: R681-R694 (1989).

Gupta, M., "Palatin, King Pharma Delay Late-Stage Trial Plans for Drug," *Reuters* Aug. 30, 2007.

Mishra, A., "Palatin Says King Pharma Ends Drug Agreement on FDA Concern," *Reuters*, Sep. 10, 2007.

Bicknell, A.B. and P.J. Lowry, "Pro-Opiomelanocortin (POMC)," *Encyclopedia of Stress*, 3:257-265 (2000).

Voisey, J., et al., "Melanocortins and Their Receptors and Antagonists," *Current Drug Targets*, 4(7): 586-597 (2003).

Fields, C.G. et al., "HBTU Activation for Automated Fmoc Solid-Phase Peptide Synthesis," *Peptide Res*., 4(2): 95-101 (1991).

Sawyer, T.K., "Discovery and Structure-Activity Relationships of Novel Alpha-Melanocyte-Stimulating Hormone Inhibitors," *Peptide Res.*, (2)1: 140-146 (1989).

Fields, G.B., et al., "Principles and Practice of Solid-Phase Peptide Synthesis," *Synthetic Peptides*, 77-183 (1992).

Bednarek et al., Selective, High Affinity Peptide Antagonists or a-Melanotropin Action at Human Melanocoritin Receptor 4: . . . J. Med. Chem. 44:3665-3672 (2001).

Giuliani et al., Selective melanocortin MC4 receptor agonists reverse haemorrhagic shock and prevent multiple organ damage, British J. Pharmacol. 150:595-603 (2007).

Han et al., De Novo Design, Synthesis, and Pharmacology of a-Melanocyte Stimulating Hormone Analogues Derived from Somatostatin . . ., J. Med. Chem. 47(6): 1514-1526 (2004).

* cited by examiner

SEQUENCE LISTING

<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: Pharmacophore

<400> SEQUENCE: 1

His Phe Arg Trp
1

<210> SEQ ID NO 2
<211> LENGTH: 6
<212> TYPE: PRT
<213> ORGANISM: Artificial Sequence
<220> FEATURE:
<223> OTHER INFORMATION: Pharmacophore
<220> FEATURE:
<221> NAME/KEY: MOD_RES
<222> LOCATION: (1)..(1)
<223> OTHER INFORMATION: ACETYLATION, Nle

<400> SEQUENCE: 2

Leu Asp His Phe Arg Trp
1               5

<210> SEQ ID NO 3
<211> LENGTH: 8
<212> TYPE: PRT
<213> ORGANISM: Artificial Sequence
<220> FEATURE:
<223> OTHER INFORMATION: Pharmacophore

<400> SEQUENCE: 3

His Phe Arg Trp Gly Lys Pro Val
1               5

STABILIZED MELANOCORTIN LIGANDS

CROSS-REFERENCE TO RELATED APPLICATIONS

This application is a national phase of International Application PCT/US10/47108, filed Aug. 30, 2010, which claims priority under 35 USC §119 to U.S. Provisional Application No. 61/238,625, filed Aug. 31, 2009, each of which is herein incorporated by reference in its entirety.

FIELD OF THE INVENTION

The present invention provides melanocortin ligands having a degradation-resistant C-terminal extension to minimize or abolish cardiovascular effects for use in the treatment of various pathological conditions.

BACKGROUND OF THE INVENTION

Description of Related Art

The following discussion refers to a number of publications by author(s) and year of publication. Discussion of such publications herein is given to present a more complete background and is not to be construed as an admission that such publications are "prior art".

Melanocortins are a group of small peptides that bind to a family of five known melanocortin receptors (MC1R through MC5R) (Cone, R. D., 2006, *Endocr. Rev.*, 27(7):736-749). They are derived from a common precursor protein, pro-opiomelanocortin (POMC), which is expressed in the neurons of the central and peripheral nervous system, and in the pituitary gland (Voisey, J et al., 2003, *Curr. Drug Targets*, 4(7):586-597). The proteolytic cleavage of POMC results in α- β- and γ-melanocortin and adrenocorticohormone (ACTH), in addition to several other biologically important peptides.

Of the five known melanocortin receptors, MC3R and MC4R are thought to be expressed predominantly in the mammalian brain, with MC3R being most highly expressed in the arcuate nucleus of the hypothalamus, and MC4R being expressed in the thalamus, hypothalamus, and hippocampus. MC1R is expressed mainly in the periphery where it is found, for example, on melanoma cells and melanocytes and immune cells. In the neuronal system, MC1R is present only on neurons in the periaqueductal grey matter of the midbrain, where it is believed to have a role in controlling pain. MC2R is predominantly expressed in the adrenal cortex, where it controls steroidogenesis. MC5R is found predominantly in peripheral tissues such as the secretory epithelia of many exocrine glands, where it affects secretory and trophic controls.

Melanocortin peptides were initially thought to have a physiological function primarily directed to the control of skin pigmentation. However, in the last 25 years, many additional biological activities have been attributed to the melanocortins. Melanocortin peptides that are either agonists (activators) or antagonists (inhibitors) have been shown to control many physiological processes, including pigmentation, feeding, overall metabolic rate/energy homeostasis, endocrine and exocrine gland secretion, inflammation, sodium excretion by the kidney, pain sensation, addictive behavior, and sexual drive.

Therefore, melanocortin analogs have been synthesized for the potential regulation and treatment of many conditions, including weight regulation (e.g., obesity, anorexia, and cachexia), hormonal secretion, and hyposecretion of many exocrine glands (e.g., Sjogren's Syndrome), immuno-relevant conditions, and sexual dysfunction (Cone, R. D., 2006, *Endocr. Rev.*, 27(7):736-749; Cone, R. D., 2005, *Nat. Neurosci*, 8(5):571-578; Bazzani, C., et al., 2002, *Resuscitation*, 52(1):109-115; and Bertonlini, A., et al., 2009, *Pharmacol. Res*, 59(1):13-47). However, in regulating these physiological effects, melanocortin analogs have also been shown to cause hypertension (Gruber, et al., 1984, *Hypertension*, 6:468-474 and Klein, et al., 1985, *Life Sci.* 36:769-775). Experimental studies have shown that administration of melanocortin analogs (ligands) increases arterial pressure and heart rate, and can produce cardiac arrhythmias (Gruber and Callahan, 1989, *Am. J. Physiol.* 257:R681-R694; and unpublished data).

The physiological regulatory effects of a melanocortin peptide are achieved through the melanocortin pharmacophore: (His-Phe-Arg-Trp) (SEQ ID NO: 1); this pharmacophore being the minimum set of amino acids necessary for melanocortin-regulated activity (Holder, J. R. and C. Haskel-Luevano, 2004, *Med. Res. Rev.*, 24(3):325-356). In general, all melanocortin peptides share the same active core sequence: His-Phe-Arg-Trp (SEQ ID NO: 1), including melanotropin neuropeptides and adrenocorticotropin. The amino acids surrounding this core sequence in naturally occurring melanocortin peptides are believed to affect the relative affinity for a specific melanocortin receptor.

Various non-naturally occurring melanocortin analogs having enhanced affinity for melanocortin receptors have been synthesized. For example, Klemes et al. 1986, *Biochem. Biophys. Res. Commun.*, 137(2):722-728 synthesized the melanocortin analogs (Ac-Nle-Asp-His-D-Phe-Arg-Trp) and (Ac-Nle-Asp-His-Phe-Arg Trp) (SEQ ID NO: 2). These modified analogs show increased potency for melanotropic activity. Several other melanocortin analogs have been identified. Further examples of melanocortin analogs that have been synthesized, having increased potency, include (Ac-Nle-cyclo-Asp-His-Phe-Arg-Trp-Lys) and (Ac-Nle-cyclo-Asp-His-D-Phe-Arg-Trp-Lys) (al-Obeidi et al., 1989, *J. Med. Chem*, 32(12):2555-2561); (Ac-Nle-cyclo-Asp-His-D-Nal 2'-Arg-Trp-Lys) and (Ac-cyclo-Cys-Glu-His-D-Nal 2'-Arg-Trp-Gly-Cys-Pro-Pro-Lys-Asp) (Balse-Srinivasan et al., 2003, *J. Med. Chem.*, 46(17):3728-3733); (Ac-Nle-Glu-His-D-Phe-Arg-D-Trp-Gly) (al-Obeidi et al., 1989, *Pept. Res.*, 2(1):140-146); and (His-Phe-Arg-Trp-Gly-Lys-Pro-Val) (SEQ ID NO: 3), (Masman et al., 2008, *Bioorg. Med. Chem.*, 16(8):4347-58).

However, due to their potent cardiovascular side effects (Greenfield et al., 2009, *N. Eng. J. Med.* 360:44-52; Gupta, 2007, *Reuters* Aug. 30, 2007; Mishra, 2007, *Reuters* Sep. 10, 2007; Nordheim et al., 2006, *Peptides* 27:438-443), the melanocortin analogs synthesized to date have not yet resulted in a governmental regulatory agency approved therapeutic drug for treating any of the many melanocortin-related conditions. The clinically unacceptable cardiovascular effects of melanocortin analogs are mediated by a second pharmacophore (Arg-Trp) located within the first pharmacophore. (Klein et al., 1985, *Life Sci.*, 36:769-775; Gruber and Callahan, 1989, *Am. J. Physiol.*, 257:R681-694). This second pharmacophore is believed to interact with a subset of the RFamide receptor family, resulting in elevation of central sympathetic drive and initiation of cardiovascular effects. The generalized motif of an Arg-aromatic di-peptide sequence at or near the C-terminus of many synthetic melanocortin ligands is a more inclusive description of the pharmacophore of the RFamide class (Gruber and Callahan, *Am. J. Physiol.*, 1989, 257:R681-694;

Klein et al., 1985, *Life Sci.* 36:769-775; Clements et al., 2001, *Biochem. Biophys. Res. Commun.*, 284:1189-1193).

Although it has long been believed that melanocortin cardiovascular effects cannot be separated from the non-hypertensive, and potentially therapeutic, physiological effects, Gruber and Callahan showed that this is incorrect. (Gruber and Callahan 1989, *Am. J. Physiol.*, 257:R681-694). Peptide C-terminal extension of a melanocortin analog can minimize acute cardiovascular activity, while preserving melanocortin effects. Effectively, the additional C-terminal amino acids temporarily "hide" the cardiovascular/RFamide-like pharmacophore (Arg-Trp) by moving it deeper within the molecular structure of the peptide. This acutely suppresses the cardiovascular effects without affecting the melanocortin activity.

Nonetheless, many of the C-terminal extensions on melanocortin analogs that have shown minimized cardiovascular activity in in vitro assays have been shown to be degraded in vivo. Melanocortin analogs having C-terminal extensions may initially confer only the desired effects, but once degradation occurs, the (Arg-Trp) RFamide pharmacophore is unmasked, conferring the associated cardiovascular effects.

SUMMARY OF THE INVENTION

Since melanocortin drugs would potentially be used to treat chronic conditions, they must not produce potentially dangerous side effects during prolonged administration. Thus, suppression of melanocortin ligand cardiovascular effects, during chronic administration, is important for a clinically safe melanocortin drug. This requires prolonged in vivo separation of the RFamide cardiovascular actions of the melanocortin pharmacophore from its therapeutic melanocortin effects. This would allow melanocortin analogs to be used as treatments for a variety of pathological conditions, with minimal risk of cardiovascular pathology. In a first aspect of the invention, a non-naturally occurring melanocortin ligand is provided and comprises a melanocortin analog coupled to a degradation-resistant C-terminal extension, effectively producing chronic separation of melanocortin from RFamide cardiovascular activity.

In a second aspect of the invention, a non-naturally occurring melanocortin ligand is provided and comprises a melanocortin analog coupled to a degradation-resistant C-terminal extension that is selected from at least one amino acid, at least one modified amino acid, a peptide mimetic, and combinations thereof.

In a third aspect of the invention, a non-naturally occurring melanocortin ligand is provided and comprises a melanocortin analog coupled to a degradation-resistant C-terminal extension and a degradation-resistant N-terminal extension.

DETAILED DESCRIPTION OF THE INVENTION

A composition is provided comprising a non-naturally occurring melanocortin ligand coupled to a degradation-resistant C-terminal extension to suppress exposure and effect of the RFamide/cardiovascular pharmacophore, and optionally an N-terminal extension to prevent N-to-C-terminus (i.e., left to right) enzymatic degradation of the melanocortin pharmacophore. The degradation-resistant C-terminal extension is at least one amino acid, at least one modified amino acid, a peptide mimetic (non-amino acid small molecule), or combinations thereof. A degradation-resistant C-terminal extension is one selected to resist degradation under physiological conditions, thereby allowing the melanocortin analog to maintain at least one melanocortin physiological regulatory effect while exhibiting minimized or abolished cardiovascular effects when acutely or chronically administered to a human or mammal.

Terminology

Melanocortin analog refers to at least a melanocortin pharmacophore. Melanocortin analogs are molecules that bind melanocortin receptors under physiological conditions. Melanocortin analogs include non-naturally occurring melanocortin polypeptides and truncated and/or modified versions of a melanocortin full-length protein or polypeptide. For example, the full-length POMC protein, prior to proteolytic cleavage of "sub-peptides," consists of 241 amino acids. Tissue-specific proteolytic cleavage of POMC yields peptides ranging in size from 13 amino acids to 76 amino acids (Bicknell and Lawry, 2000, *Encyclopedia of Stress,* vol. 3, 257-265, Academic Press). Synthesized, non-naturally occurring melanocortin analogs having increased melanocortin receptor activity as discussed herein are approximately 7-12 amino acids in size. Melanocortin analogs exhibit binding functionality with melanocortin receptors. The binding is either activating (agonist) or inhibitory (antagonist). In addition to peptides, the melanocortin analogs include small molecule analogs of melanocortin or a portion thereof comprised of organic or inorganic compounds or a combination of peptide and small molecule—i.e., peptide mimetics.

The melanocortin analogs can be structurally similar and/or functionally similar to the melanocortin proteins in their ability to bind melanocortin receptors. Further, the melanocortin analogs generally contain the pharmacophore: His-Phe-Arg-Trp (SEQ ID NO: 1) or a modified version thereof, or a structural or functional peptide mimetic thereof.

Peptide mimetic is a non-amino acid molecule that mimics a peptide (a chain of amino acids) or one amino acid residue.

Pharmacophore is the minimum set of amino acid residues necessary to achieve a physiological effect; or a small molecule that is (with respect to a receptor) a structural mimic of the amino acid residues required for binding to and activation of a receptor. His-Phe-Arg-Trp (SEQ ID NO: 1) and their analogs are the pharmacophore of melanocortin for the regulated physiological effect. Therefore, non-naturally occurring melanocortin pharmacophore analogs can be small peptides or organic molecules designed to mimic the appearance or function (including activation or deactivation of receptor activity) of the melanocortin pharmacophore core sequence peptide.

Cardiovascular effects include the medical definition of hypertension, namely that of high blood pressure (at least above 120/80 mm Hg, and especially if above 140/90 mm Hg (systolic/diastolic), pathological effects on the vasculature, kidney and heart, and other associated effects. Conversely, hypotension is when the blood pressure drops below medically accepted nouns. Cardiac arrhythmias imply an alteration in the normal symmetrical appearance of the pulsatile pressure wave of arterial pressure. This can be increased beats per minute (tachycardia) or decreased beats per minute (bradycardia). It also may imply an alteration in the normal wave pattern of the electrocardiogram.

Substantial degradation refers to the degradation of the C-terminal extension, the N-terminal extension, or other regions of the melanocortin analog of the melanocortin ligand of the present invention, by physiological enzymes and other factors, in such a manner or to a degree that the RFamide pharmacophore is again capable of initiating a cardiovascular effect through the RFamide receptor or other physiological systems, comparable to melanocortin ligands or melanocortin analogs without a C-terminal extension. According to a preferred aspect of the invention, a melanocortin analog having a C-terminal extension that resists substantial degradation is one in which no more than 50% of the administered ligand can reestablish a cardiovascular effect, preferably no more than 25%, and more preferably less than 10%, as compared to a melanocortin analog that lacks a C-terminal extension.

A pharmaceutical composition includes a ligand of this invention, or a pharmaceutically acceptable salt thereof, and a pharmaceutically acceptable carrier. The carrier may be a liquid formulation, for example, a buffered, isotonic, aqueous solution. Pharmaceutically acceptable carriers also can include excipients, such as diluents, carriers and the like, and additives, such as stabilizing agents, preservatives, solubilizing agents, buffers and the like.

A pharmaceutically acceptable salt refers to a salt prepared from pharmaceutically acceptable non-toxic bases or acids, including inorganic and organic acids and bases. Salts derived from inorganic bases include aluminum, ammonium, calcium, copper, ferric, ferrous, lithium, magnesium, manganic, manganous, potassium, sodium, zinc, and similar salts. Particularly preferred are ammonium, calcium, lithium, magnesium, potassium, and sodium salts. Salts derived from pharmaceutically acceptable, organic, non-toxic bases include salts of primary, secondary, and tertiary amines, substituted amines, including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and similar basic ion exchange resins.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and similar acids. Particularly preferred are citric, fumaric, hydrobromic, hydrochloric, maleic, phosphoric, sulfuric, and tartaric acids.

It will be understood that, as used herein, references to the compounds of Formula I and Formula II are meant to also include the pharmaceutically acceptable salts of these compounds, such as hydrochloride salts, etc.

Abbreviations in the listing of compounds have their conventional meaning. Thus, "Nle" is norleucine; "Nal" is noralanine; "D-Nal" is D-noralanine; "Asp" is aspartic acid; "His" is histidine; "D-Phe" is D-phenylalanine; "Arg" is arginine; "Trp" is tryptophan; "Lys" is lysine; "Gly" is glycine; "Pro" is proline; "Tyr" is tyrosine; "Ser" is serine; "Cys" is cysteine; "Val" is valine; "D/L-Thr" is either D-threonine or L-threonine; "D/L-Pro" is either D-proline or L-proline. Additionally, "Ac" is N-acetyl and "cyclo" refers to a cyclic structure, which is also shown in the literature as "c" or referred to as a "lactam".

Additional abbreviations are defined as follows: Nal(2')=D-2'-naphthylalanine; tBu=tert-butyl; Hyp(Bzl)=benzyl-L-hydroxy-proline; Mamb=3-aminomethyl-benzoic acid; glutaric acid linker=CO—(CH$_2$)$_3$—CO; Pen=L-Penicillamine; Aib=2-Aminoisobutyric acid; Tic=1, 2,3,4-Tetrahydroisoquinoline-3-carboxylic Acid; Aba=4-amino-1,2,4,5-tetra-hydro-2-benzazepin-3-one; Pip=piperidine-2-carboxylic acid; Nip=piperidine-3-carboxylic acid; Tic=tetrahydroquinoline-3-carboxylic acid; Bip=biphenylalanine; Phg=α-Phenyl-glycine; Sar=Sarcosine; Azt=3'-azido-3'-deoxythymidine; Oic=Octohydroindole-2-carboxylic acid.

Melanocortin Analog

In one embodiment, a non-naturally occurring melanocortin ligand is represented by Formula I as shown, and comprises a melanocortin analog coupled to a degradation-resistant C-terminal extension and an optional N-terminal extension:

$$Y^1\text{-}Y^2\text{-}Y^3\text{-}R^1\text{-}R^2\text{-}R^3\text{-}R^4\text{-}R^5\text{-}R^6\text{-}R^7\text{-}X^1\text{-}X^2\text{-}X^3 \quad \text{(Formula I)}$$

wherein $Y^1\text{-}Y^2\text{-}Y^3$ represents optional stabilizing N-terminal residues or an amino acid residue mimetic; $R^1$ to $R^7$ represent residues of the melanocortin analog; and $X^1\text{-}X^2\text{-}X^3$ represent degradation-resistant C-terminal residues or an amino acid residue mimetic.

Collectively, $R^1$ to $R^7$ ($R^1\text{-}R^2\text{-}R^3\text{-}R^4\text{-}R^5\text{-}R^6\text{-}R^7$) can be one of many known melanocortin analogs, wherein each of the seven residues is independently an amino acid or peptide mimetic. Some melanocortin analogs have less than seven residues. In another embodiment, $R^1$ to $R^7$, collectively, represent alpha melanocortin analogs. In another embodiment, $R^1$ to $R^7$, collectively, represent melanocortin analogs which bind to MC3-MC5 receptors as agonists or antagonists.

In one embodiment, the melanocortin ligand is represented by Formula I above, and residues $R^1$ to $R^7$, collectively, represent the melanocortin analog, wherein $R^1$ is absent or is selected from the group consisting of cysteine, norleucine, acetylated norleucine, acetylated cysteine, D-phenylalanine, methylated D-phenylalanine, succinic acid, o-pthalic acid, tyrosine, aspartic acid, glutaric acid, CO-cis-CH=CH—CO, an n-pentanoyl group, and an n-hexanoyl group;

$R^2$ is absent or is selected from the group consisting of proline, aspartic acid, glutamic acid, glycine, cysteine, norleucine, arginine, succinic acid, glutaric acid, CO-cis-CH=CH—CO, an n-pentanoyl group, and an n-hexanoyl group;

$R^3$ is selected from the group consisting of histidine, histidine methylated at positions 1 or 3, D-proline, L-proline, D-Nal(2'), L-Nal(2'), succinic acid, tButGly, Hyp(Bzl), Mamb, Oic, norleucine, Aba, β-alanine, and Tic;

$R^4$ is selected from the group consisting of histidine, D-phenylalanine, L-phenylalanine, D-Nal(2'), pCl-D-Phe, and (o-Phe)Phe;

$R^5$ is selected from the group consisting of arginine, homoarginine, ornithine, alanine, proline, Pip, Nip, Tic, Phg, Sar, and Azt;

$R^6$ is selected from D-tryptophan, L-tryptophan, D-Nal (2'), L-Nal(2'), Tic, and Bip;

$R^7$ is absent or is selected from the group consisting of glycine, glutamic acid, cysteine, lysine, and 2,3-diaminopropionic acid;

wherein if $R^3$ is Aba, then $R^4$ is selected from the group consisting of D-Phe, D-Nal(2'), and pCl-D-Phe; and wherein if $R^2$ is an n-pentanoyl group or an n-hexanoyl group, then $R^1$, $Y^1$, $Y^2$, and $Y^3$ are absent.

In another embodiment, the melanocortin ligand of the present invention is represented by Formula II:

$$Y^1\text{-}Y^2\text{-}Y^3\text{-}R^1\text{-}R^2\text{-}R^3\text{-}R^4\text{-}R^5\text{-}R^6\text{-}R^7\text{-}R^8\text{-}R^9\text{-}X^1\text{-}X^2\text{-}X^3 \quad \text{(Formula II)}.$$

Collectively, $R^1$ to $R^9$ ($R^1\text{-}R^2\text{-}R^3\text{-}R^4\text{-}R^5\text{-}R^6\text{-}R^7\text{-}R^8\text{-}R^9$) can be one of many known melanocortin analogs, wherein each of the nine residues is an amino acid or peptide mimetic. Some melanocortin analogs have less than nine residues. In another embodiment, $R^1$ to $R^9$, collectively, represent gamma melanocortin analogs. In another embodiment, $R^1$ to $R^9$, collectively, represent melanocortin analogs which bind to MC3 receptors as antagonists.

In one embodiment, the melanocortin ligand is represented by Formula II above, and residues $R^1$ to $R^9$, collectively, represent the melanocortin analog, wherein:

$R^1$ is tyrosine;

$R^2$ is valine;

$R^3$ is selected from the group consisting of methionine, norleucine, cysteine, and L-penicillamine;

$R^4$ is selected from the group consisting of glycine, D-cysteine, L-cysteine, aspartic acid, and norleucine;

$R^5$ is selected from the group consisting of histidine, norleucine, proline, and Aib;

$R^6$ is selected from the group consisting of phenylalanine, D-Nal(2'), and L-Nal(2');

$R^7$ is arginine;

$R^8$ is selected from the group consisting of tryptophan and D-Nal(2'); and $R^9$ is absent or is selected from the group consisting of aspartic acid, cysteine, penicillamine, and lysine.

In another embodiment, a melanocortin ligand represented by Formula I or Formula II is provided, wherein at least one D-phenylalanine residue, or all D-phenylalanine residues are halogenated (e.g., fluorine or chlorine) to confer improved melanocortin protein-ligand interaction with its corresponding MC receptor(s) (Ippolito, J. A and D. W. Christianson, 1992, *Int. J. Biol. Macromol,* 14(4):193-197.)

C-Terminal Extension

To the $R^1$ to $R^7$ melanocortin analog of Formula I, or to the $R^1$ to $R^9$ ($R^1$-$R^2$-$R^3$-$R^4$-$R^5$-$R^6$-$R^7$-$R^8$-$R^9$) melanocortin analog of Formula II, a C-terminal extension is provided in order to confer degradation-resistance of the C-terminal extension to prevent exposure of the RFamide sequence.

In one embodiment, the C-terminal extension is represented by $X^1$-$X^2$-$X^3$ of Formula I, wherein $X^1$ is selected from the group consisting of cysteine, D-threonine, L-threonine, D-proline, L-proline, and a piperazin-2-one ring;

$X^2$ is absent or is selected from the group consisting of D-threonine, L-threonine, D-proline, L-proline, and a piperazin-2-one ring; and $X^3$ is absent or is selected from the group consisting of D-threonine, L-threonine, and a piperazin-2-one ring.

In another embodiment, the C-terminal extension is represented by $X^1$-$X^2$-$X^3$ of Formula II, wherein $X^1$ is selected from the group consisting of cysteine, D-threonine, L-threonine, D-proline, L-proline, and a piperazin-2-one ring;

$X^2$ is absent or is selected from the group consisting of D-threonine, L-threonine, D-proline, L-proline, and a piperazin-2-one ring; and $X^3$ is absent or is selected from the group consisting of D-threonine, L-threonine, and a piperazin-2-one ring.

In one embodiment, the C-terminal extension has a conformation that chronically inhibits degradation from carboxy peptidases. Examples of a C-terminal extension that chronically inhibit degradation include the di-and tripeptides of D-Pro-D-Pro, D-Thr-D-Pro, D-Thr-D-Pro-D-Thr, as described in Tugyi et al., 2005, *Proc. Nat. Acad. Sci.* (USA), 102(2):413-418.

In another embodiment, a proline mimetic (piperazin-2-one ring) is substituted for D-Pro. In one approach, a proline mimetic is synthesized as described by Teixido, M., et al., 2007, *Brain Res. Bull.,* 73(1-3):103-107. The piperazin-2-one ring is also discussed in Bhatt, U. and Just, G., 2000, *Helvetica Chimica Acta,* 83:722-727. For the replacement of proline with a piperazin-2-one ring, an ethylene bridge is incorporated between the nitrogen molecules of two adjacent α-amino groups. This produces a six-membered ring, containing two nitrogen and four carbon atoms, a structure that is similar to a proline ring (albeit six-membered) between the two adjacent amino acid residue functional groups.

In accordance with the teaching of the present invention, the C-terminal extension of the melanocortin analog is resistant to substantial degradation prior to the ligand being cleared from the bloodstream in the human or animal body. In one embodiment, a C-terminal extension is of sufficient stability such that the melanocortin ligand does not cause cardiovascular effects, or has minimized cardiovascular effects when administered to a human or animal. As stability of peptides, amino acids, and small molecules varies widely, melanocortin ligands of the present invention have variable length C-terminal extensions in the extracellular physiological environment. The C-terminal extension is of sufficient stability (e.g., length, steric structure) such that any degradation in the body prior to its clearance from the bloodstream will not re-expose the cardiovascular pharmacophore to achieve its effect.

N-Terminal Extension

In one embodiment of the present invention, an N-terminal extension is coupled to the melanocortin analog. The N-terminal extension is represented as $Y^1$-$Y^2$-$Y^3$ in Formula I, wherein $Y^1$ is absent or is selected from the group consisting of D-threonine, L-threonine, D-proline, and L-proline;

$Y^2$ is absent or is selected from the group consisting of D-threonine, L-threonine, D-proline, L-proline, and a piperazin-2-one ring; and $Y^3$ is absent or is selected from the group consisting of cysteine, D-threonine, L-threonine, D-proline, L-proline, and a piperazin-2-one ring.

In another embodiment, an N-terminal extension is represented as $Y^1$-$Y^2$-$Y^3$ in Formula II, wherein $Y^1$ is absent or is selected from the group consisting of D-threonine, L-threonine, D-proline, and L-proline;

$Y^2$ is absent or is selected from the group consisting of D-threonine, L-threonine, D-proline, L-proline, and a piperazin-2-one ring; and $Y^3$ is absent or is one selected from the group consisting of cysteine, D-threonine, L-threonine, D-proline, L-proline, and a piperazin-2-one ring.

Cyclization of the Melanocortin Ligand of Formula I

Cyclized melanocortin analogs have shown improved efficacy and stability (Balse-Srinivasan et al., 2003, *J. Med. Chem.,* 46(17):3728-3733 and Bednarek et al., 2001, *Biochem. Biophys. Res. Commun.,* 286(3):641-645; Kavarana, et al., 2002, *J. Med. Chem.,* 45(12):2644-2650). In one embodiment, the non-naturally occurring melanocortin ligand represented by Formula I is cyclized. The following represents a non-limiting list of examples of how the melanocortin ligand represented by Formula I can be cyclized:

A disulfide bond between $R^1$ or $R^2$ and $R^7$ or $X^1$ when $R^1$ or $R^2$ is cysteine and $R^7$ or $X^1$ is cysteine, as described in Balse-Srinivasan et al., 2003, *J. Med. Chem.,* 46(23):4965-4973. When $X^1$ is cysteine, $X^2$ is not absent, but is selected from the group consisting of D-threonine, L-threonine, D-proline, L-proline and a piperazin-2-one ring.

A lactam bridge between $R^1$ and $R^7$ when $R^1$ is norleucine and $R^7$ is glutamic acid, as described in Mayorov et al., 2006, *J. Med. Chem.,* 49:1946-1952, and Bednarek et al., 2001, *Biochem Biophys. Res. Commun.,* 286(3):641-645.

A side-chain lactam bridge between $R^2$ and $R^7$ when $R^2$ is glutamic acid or aspartic acid and $R^7$ is lysine, as described in Bednarek et al., 2001 *Biochem Biophys. Res. Commun.*, 286 (3):641-645.

A lactam closure between $R^1$ and $R^7$ when $R^1$ is succinic acid or o-pthalic acid and $R^7$ is lysine, as described in Bednarek et al., 2001, *Biochem Biophys. Res. Commun.*, 286 (3):641-645 and Kavarana, et al., 2002, *J. Med. Chem.*, 45(12):2644-2650.

A lactam closure between $R^2$ or $R^3$ and $R^7$ when $R^2$ or $R^3$ is succinic acid and $R^7$ is 2,3-diamino-propionic acid as described in Bednarek et al., 2001, *Biochem Biophys. Res. Commun.*, 286(3):641-645.

A "backbone" cyclized peptide is formed by covalent bond formation between the N and/or C terminus of a linear peptide of interest. An example of this is described in the bonding of two amide nitrogens via a bridge consisting of alkyl groups and an amide, as described by Hess et al., 2007, *J. Med. Chem.*, 50:6201-6211.

Amino Acids—Isomers and Non-Standard Amino Acids

In one embodiment, the amino acid residues, as provided herein for the non-naturally occurring melanocortin ligand of the present invention, can be either D- or L-amino acids or can be substituted with their non-standard, isomeric counterparts. For example, alpha amino acids can be substituted with beta amino acids, and L amino acids can be substituted with D amino acids. An amino acid disclosed herein that is not designated as a D- or L-isomer, can be either isomer.

Cyclization of the Melanocortin Ligand of Formula II

In another embodiment, the non-naturally occurring melanocortin ligand represented by Formula II is cyclized. The melanocortin analog represented by Formula II can be cyclized through a lactam side chain between $R^4$ and $R^9$ when $R^4$ is aspartic acid and $R^9$ is lysine, as described (Bednarek et al., 2001, *Biochem. Biophys. Res. Commun.*, 286(3):641-645 and Mayorov et al., 2006, *J. Med. Chem.*, 49:1946-1952.

Melanocortin Ligands for MC Receptor Binding

In one embodiment, the non-naturally occurring melanocortin ligand of the present invention is an MC4 receptor agonist, an MC4 receptor antagonist, an MC3 receptor agonist, an MC3 receptor antagonist, and/or an MC5 agonist, of the alpha melanocyte-stimulating hormone (MSH) group.

In another embodiment, the non-naturally occurring melanocortin ligand of the present invention is an MC3 antagonist of the gamma melanocyte-stimulating hormone group.

In another embodiment, the non-naturally occurring melanocortin ligand of the present invention is an MC3 agonist of the gamma melanocyte-stimulating hormone group.

Synthesis of Peptides and Extensions

In general, the melanocortin ligands disclosed are synthesized by solid-phase synthesis, for example, and purified according to methods known in the art. A number of well-known procedures utilizing a variety of resins and reagents are used to prepare the compounds of this invention. Organic molecules are similarly synthesized according to methods known in the art.

Ligands of this invention may be in the form of any pharmaceutically acceptable salt. Acid addition salts of the ligands of this invention are prepared in a suitable solvent from the molecule and an excess of an acid, such as hydrochloric, hydrobromic, sulfuric, phosphoric, acetic, trifluoroacetic, maleic, succinic, or methanesulfonic. Where the ligands include an acidic moiety, suitable pharmaceutically acceptable salts may include alkali metal salts, such as sodium or potassium salts, or alkaline earth metal salts, such as calcium or magnesium salts.

In one embodiment, peptides are prepared by solid-phase methodology by using p-benzyloxy-benzylalcohol resin for free C-terminus peptides with manual synthesis. All amino acids are coupled as 9-fluroenylmethoxycarbonyl (Fmoc)-derivatives, as described by Fields et al., 1992, *Synthetic Peptides: A User's Guide,* W.H. Freeman and Company, New York, 77-183; and Fields and Noble, 1990, *Int. J. Peptide Protein Res.*, 35:161-214; Fields et al., 1991, *Peptide Res.* 4:95-101. In brief, the tert-butyl group is applied as a protecting group for 1-hydroxybenzotriazole/N,N'diisopropylcarbodiimide in situ active ester methodology in N,N-dimethylforaminide (DMF). Fmoc groups are removed by 20% piperidine in DMF, or 2% piperidine and 2% diazabicyclo[5.4.0]undec-7-ene in DMF, respectively. The success of the coupling and deprotection is monitored by ninhydrin test and/or isatine assay. After the completion of the synthesis, the peptides are cleaved from the resin with trifluoroacetic acid containing 5% water. The crude products are purified by RP-HPLC on a Supelcosil C18 column by using gradient elution with the following eluents: A, 0.1% trifluoroacetic acid in water; and B, 0.1% trifluoroacetic acid in acetonitrile/water (80:20, vol/vol). After an isocratic elution with over 5% eluent B for 5 min, a linear gradient from 0-25% B or 5-30% B is generated over 25 minutes at room temperature and with a flow rate of 4 mL/min. UV detection is performed at lambda=214 nm. The purity of the peptides is investigated by analytical RP-HPLC on a Synergi (4.6 mm×25 cm, MAX-RP 80 Angstrom, 4 μm) column.

The following references disclose methods for synthesizing the residues and linkages embodied in this invention. For the piperizin-2-one ring—see Bhatt, U and Just, G, 2000, *Helvetica Chimica Acta,* 83:722-727; Mohamed, N., et al., 1998, *Tetrahedron Lett.,* 39:8213-8216; Teixido, M., et al., 2007, *Brain Res. Bull.,* 73(1-3):103-107. For Nal(2')—see Kavarana, M J et al., 2000, *J. Med. Chem.,* 45:2644-22650; and Holder, J. R., et al., 2002, *J. Med. Chem.,* 45:5736-5744. For the dipeptide mimetics of Aba-D-Phe, Aba-pCL-D-Phe, and Aba-D-Nal(2')—see Ballet, S., et al., *Bioorganic & Med. Chem. Lett.,* 2007, 17:2492-2498. For OIC, BIP and PIP—see Bednarek, M. A., et al., 2007, *J. Med Chem,* 50:2520-2526. For glutaric acid linker—see Mayorov, A. V. et al., 2008, *J. Med. Chem.* 51:187-195. For Hyp(Bzl), t-butylglycine, and MAMB—see Grieco, P., et al., 2007, Peptides 28:1191-1196. For Azt, Pip, Nip, Tic, Oic—see Bednarek, M. A., 2007, *Chem. Biol. Drug Design,* 69:350-355. For lactam cyclization—see Mayorov, A. V,. et al., 2006, *J. Med. Chem.* 49:1946-1952. For Pen and Aib—see Balse-Srinivasan. P., et al., 2003 *J. Med. Chem,* 46:4965-4973. For an n-pentanoyl group and n-hexanoyl group—see Cheung A. W. -H., et al., 2003, *Bio-organic & Med. Chem. Lett.,* 13:1307-1311. ORN (ornithine) and homoArg—see Holder, J. R. et al., 2003, *Peptides,* 24:73-82. For Phg—see Holder, J. R. et al., 2002, *J. Med. Chem.,* 45, 3073-3081. For 2,3 diaminopropionic acid—see 2004, Vig, B. S., et al., *J. Med. Chem.,* 47(2):446-455.

Assaying Cardiovascular Effects Using Melanocortin Ligand of the Present Invention There are many possible methods that would be known, obvious, or available to the skilled person for directly and indirectly assaying the degradation and cardiovascular effects of a melanocortin ligand of the present invention.

Both acute and chronic cardiovascular testing are assayed using the melanocortin ligands of the present invention in order to determine if the C-terminal extensions as described herein can protect the RF-pharmacophore from exposure. In this way, the C-terminal degradation resistance is measured indirectly, but in a therapeutically applicable manner. Furthermore, with both the acute and chronic cardiovascular measurements, the cardiovascular effects are then known upon introduction/administration of the melanocortin ligand into a human or mammal, and until the melanocortin ligand is cleared from the bloodstream of the human or mammal body. Acute cardiovascular recordings allow for a continuous analysis of the actions of these drugs over a period of hours, allowing for intensive observation of effects following ligand administration. The cardiovascular parameters for acute cardiovascular testing include: direct arterial pressure components (systolic, diastolic, mean arterial pressure, and heart rate) and the EKG. The arterial pressure components are measured via a Millar solid state pressure transducer in the femoral artery. This allows for a more precise evaluation of any arterial pressure/heart rate abnormalities. The signal from the Millar transducer is amplified in a Transonic arterial pressure module, and then sent to a computer running EMKA software (EMKA Technologies, Inc., Falls Church, Va.). Arterial pressure component signals are typically measured on a second-to-second basis, although millisecond or beat-by-beat analysis is an alternative measurement. The latter analysis can be performed retrospectively, via an experiment play-back. Initially, arterial pressure components to be analyzed include peak MAP (mean arterial pressure) and HR (heart rate) responses, and the areas under each respective curve. Because melanocortin analogs having exposed RF pharmacophores produce prolonged and variable pressor and cardioaccelerator actions, the area under each curve (AUC) is calculated (see, for example, D'Angelo et al., 2005, *Am. J. Physiol. Heart Circ. Physiol.*, 288(4):H1829-H1835), as are the first and second derivatives for the equations describing each cardiovascular parameter curve. For chronic cardiovascular testing, telemetry systems allow for the monitoring of multiple animals over long periods of time (days or weeks). Each animal is only recorded for a few seconds (e.g., 5-10 sec) per minute to maximize battery life and allow multiple animals to be monitored. However, newer models now allow for wireless recharging of implanted transmitters. One telemetry model for chronic cardiovascular testing is described below.

A telemetry system can be used for simultaneous and continuous monitoring with direct input to a computer running EMKA ecgAuto-Cardio2+. In this approach a telemetry transmitter is surgically implanted, using aseptic procedures, into the abdominal cavity of a rat. During surgery, the catheter of the transmitter is inserted into the abdominal aorta and secured with tissue adhesive. Telemetry unit ECG electrodes are sutured subcutaneously onto the upper right chest muscle and upper left abdominal wall muscle. These units simultaneously provide ECG and arterial pressure signals. Animals are typically allowed 7-10 days of surgical recovery, using return of the circadian rhythmicity of arterial pressure and HR as an objective metric. For acute experiments, a femoral IV line is tunneled to the upper back, exteriorized, and stored within a steel button assembly, sutured to the animal's back. The transmitter will produce an arterial pressure signal (via a cannulated abdominal aorta) and an ECG signal using the lead II configuration. For this, leads are implanted under the musculature of the upper right quadrant of the chest, and within the musculature of the upper left abdominal region. These procedures are well described in the literature (Stieber et al., 2006, *Mol. Pharmacol.*, 69(4): 1328-37), as well as the manufacturer's procedures.

For chronic administration of the melanocortin ligand into a rat model, both Alza minipumps for IV infusion and sustained release pellets are used (Strader, A. D., et al., 2007, *J. Pharmacol. Exp. Ther.*, 322(3): 1153-1161; and Innovative Research of America, Sarasota, Fla.). The starting effective daily dose for a melanocortin ligand of the present invention is 1 mg/kg/day for 14 days, and is titrated up to 10 mg/kg per day. As a control for drug degradation in the minipumps, parallel incubated (37° C.) controls were run and assessed for any peptide breakdown by high performance liquid chromatography (HPLC).

Methods of administration include injection, oral, nasal, and mucosal administration. If the administration is by injection, the injection may be intravenous, subcutaneous, intramuscular, intraperitoneal, or other means known in the art. The melanocortin ligand of this invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants, and other agents known in the art. Nasal administration includes any form of intranasal administration of a melanocortin ligand of this invention. A melanocortin ligand of this invention may be in an aqueous solution, such as a solution including saline, citrate, or other common excipients or preservatives. The melanocortin ligand may also be in a dry, powder or lyophilized formulation.

Reduced cardiovascular effects (blood pressure and arrhythmias) are relative in the human or animal when administered with different melanocortin ligands of the present invention. It is reduced relatively when compared between a melanocortin ligand having a C-terminal extension according to the present invention versus its counterpart without a C-terminal extension.

A pharmaceutical composition and/or a kit comprising the melanocortin ligand of the present invention is used to regulate and treat many conditions ranging from weight regulation (e.g., obesity, anorexia, and cachexia), hormonal secretion, exocrine gland hypersecretion), immuno-relevant conditions, and sexual dysfunction.

Applications

Physiological regulatory effects of a melanocortin ligand of the present invention, ranging from hormonal, neuronal, enzymatic and other extracellular and intracellular mechanisms further affect bodily conditions such as weight regulation (e.g., obesity, anorexia, and cachexia), hormonal secretion (e.g., dry eye and/or dry mouth syndrome), as well as immuno-relevant conditions and sexual dysfunction. The dysfunction of many of these physiological mechanisms leads to disease. In the present application, physiological regulatory effects are distinguishable and apart from cardiovascular effects.

In one embodiment, physiological regulatory effects of a melanocortin ligand of the present invention are rendered using agonist melanocortin analogs (al-Obeidi et al., *J. Med Chem*, 1989, 32(12), 2555-2561). In another embodiment, physiological regulatory effects are rendered using antagonist melanocortin analogs (Hruby et al., 1995, *J. Med. Chem.*, 38:3454-3461; Jayawickreme et al., 1994, *J. Biol. Chem.*, 269:29846-29854).

In summary, a non-naturally occurring melanocortin ligand is provided, comprised of a melanocortin analog coupled to a degradation-resistant C-terminal extension and, optionally, an N-terminal extension, to produce a stable melanocortin ligand having diminished or abolished cardiovascular activity while retaining desired melanocortin regulatory activity.

All references cited in the application are incorporated in their entirety as if explicitly recited herein, particularly all references directed to methodologies of synthesis.

What is claimed is:

1. A non-naturally occurring melanocortin ligand comprising a melanocortin analog coupled to a degradation-resistant C-terminal extension and an N-terminal extension, the non-naturally occurring melanocortin ligand comprising Formula I:

$$Y^1\text{-}Y^2\text{-}Y^3\text{-}R^1\text{-}R^2\text{-}R^3\text{-}R^4\text{-}R^5\text{-}R^6\text{-}R^7\text{-}X^1\text{-}X^2\text{-}X^3 \quad \text{(Formula I)}$$

wherein the melanocortin analog comprises $R^1$ to $R^7$, wherein:

$R^1$ is absent or is selected from the group consisting of cysteine, norleucine, acetylated norleucine, acetylated cysteine, acetylated D-phenylalanine, succinic acid, o-phthalic acid, tyrosine, aspartic acid, glutaric acid, CO-cis-CH=CH—CO, an n-pentanoyl group, and an n-hexanoyl group;

$R^2$ is absent or is selected from the group consisting of proline, aspartic acid, glutamic acid, glycine, cysteine, norleucine, arginine, succinic acid, glutaric acid, CO-cis-CH=CH—CO, an n-pentanoyl group, and an n-hexanoyl group;

$R^3$ is selected from the group consisting of histidine, histidine methylated at positions 1 or 3, D-proline, L-proline, D-Nal(2'), L-Nal(2'), succinic acid, tButGly, Hyp(Bzl), Mamb, Oic, norleucine, Aba, β-alanine, and Tic;

$R^4$ is selected from the group consisting of histidine, D-phenylalanine, L-phenylalanine, D-Nal(2'), pCl-D-Phe, and (o-Phe)Phe;

$R^5$ is selected from the group consisting of arginine, homoarginine, ornithine, alanine, proline, Pip, Nip, Tic, Phg, Sar, and Azt;

$R^6$ is selected from D-tryptophan, L-tryptophan, D-Nal(2'), L-Nal(2'), Tic, and Bip;

$R^7$ is absent or is selected from the group consisting of glycine, glutamic acid, cysteine, lysine, and 2,3-diamino-propionic acid;

wherein if $R^3$ is Aba, then $R^4$ is selected from the group consisting of D-Phe, D-Nal(2'), and pCl-D-Phe; and wherein if $R^2$ is an n-pentanoyl group or an n-hexanoyl group, then $R^1$, $Y^1$, $Y^2$, and $Y^3$ are absent;

wherein the degradation-resistant C-terminal extension comprises $X^1$ to $X^3$:

$X^1$ is selected from the group consisting of cysteine, D-threonine, D-proline, and L-proline and a piperazin-2-one ring;

$X^2$ is absent or is selected from the group consisting D-threonine, D-proline, L-proline, and a piperazin-2-one ring;

X³ is absent or is selected from the group consisting of D-threonine, and a piperazin-2-one ring; and wherein when X¹ is cysteine, X² is not absent;

wherein the N-terminal extension comprises Y¹ to Y³:

Y¹ is absent or is selected from the group consisting of D-threonine, L-threonine, D-proline, and L-proline;

Y² is absent or is selected from the group consisting of D-threonine, L-threonine, D-proline, L-proline, and a piperazin-2-one ring;

Y³ is absent or is selected from the group consisting of cysteine, D-threonine, L-threonine, D-proline, L-proline, and a piperazin-2-one ring; and wherein the melanocortin ligand is cyclized through a moiety selected from the group consisting of:

a disulfide bond between R¹ or R² and R⁷ or X¹ when R¹ or R² is cysteine and R⁷ or X¹ is cysteine;

a lactam bridge between R¹ and R⁷ when R¹ is norleucine and R⁷ is glutamic acid;

a side-chain lactam bridge between R² and R⁷ when R² is glutamic acid or aspartic acid and R7 is lysine;

a lactam closure between R¹ and R⁷ when R¹ is succinic acid or o-phthalic acid and R⁷ is lysine; and a lactam closure between R² or R³ and R⁷ when R² or R³ is succinic acid and R⁷ is 2,3-diamino-propionic acid.

2. A non-naturally occurring melanocortin ligand comprising a melanocortin analog coupled to a degradation-resistant C-terminal extension and an N-terminal extension, the non-naturally occurring melanocortin ligand comprising Formula II:

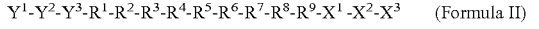

Y¹-Y²-Y³-R¹-R²-R³-R⁴-R⁵-R⁶-R⁷-R⁸-R⁹-X¹-X²-X³ (Formula II)

wherein the melanocortin analog comprises R¹ to R⁹, wherein:

R¹ is tyrosine;

R² is valine;

R³ is selected from the group consisting of methionine, norleucine, cysteine, and L-penicillamine;

R⁴ is selected from the group consisting of glycine, D-cysteine, L-cysteine, aspartic acid, and norleucine;

R⁵ is selected from the group consisting of histidine, norleucine, proline, and Aib;

R⁶ is selected from the group consisting of phenylalanine, D-Nal(2'), and L-Nal(2');

R⁷ is arginine;

R⁸ is selected from the group consisting of tryptophan and D-Nal(2'); and

R⁹ is absent or is selected from the group consisting of aspartic acid, cysteine, penicillamine, and lysine;

wherein the N-terminal extension comprises Y¹ to Y³:

Y¹ is absent or is selected from the group consisting of D-threonine, L-threonine, D-proline, and L-proline;

Y² is absent or is selected from the group consisting of D-threonine, L-threonine, D-proline, L-proline, and a piperazin-2-one ring;

Y³ is absent or is selected from the group consisting of cysteine, D-threonine, L-threonine, D-proline, L-proline and a piperazin-2-one ring;

wherein the degradation-resistant C-terminal extension comprises X¹ to X³:

X¹ is selected from the group consisting of cysteine, D-threonine, L-threonine, D-proline, L-proline, and a piperazin-2-one ring;

X² is absent or is selected from the group consisting of D-threonine, L-threonine, D-proline, L-proline, and a piperazin-2-one ring; and X³ is absent or is selected from the group consisting of D-threonine, L-threonine, and a piperazin-2-one ring; and wherein the melanocortin ligand is cyclized through a lactam side chain between R⁴ and R⁹ when R⁴ is aspartic acid and R⁹ is lysine.

3. The non-naturally occurring melanocortin ligand of claim 1, wherein the melanocortin analog is an MC4 receptor agonist, an MC4 receptor antagonist, an MC3 receptor agonist, an MC3 receptor antagonist, and/or an MC5 agonist.

4. The non-naturally occurring melanocortin ligand of claim 2, wherein the melanocortin analog is an MC3 antagonist.

5. The non-naturally occurring melanocortin ligand of claim 1, wherein D-phenylalanine is halogenated at the para position when R⁴ is D-phenylalanine.

6. A pharmaceutical composition comprising the non-naturally occurring melanocortin ligand of claim 1 and a pharmaceutical salt.

7. The pharmaceutical composition of claim 6, wherein any cardiovascular effects are diminished.

8. The pharmaceutical composition of claim 6, wherein the non-naturally occurring melanocortin ligand is AcNle-c[Asp-Pro-D-Nal(2')-Arg-Trp-Lys]-D-Thr-D-Pro-D-Thr.

9. A pharmaceutical composition comprising the non-naturally occurring melanocortin ligand of claim 2 and a pharmaceutical salt.

10. The pharmaceutical composition of claim 9, wherein any cardiovascular effects are diminished.

11. The pharmaceutical composition of claim 9, wherein the non-naturally occurring melanocortin ligand is Tyr-Val-Nle-c[Asp-Pro-D-Nal(2')-Arg-Trp-Lys]-D-Thr-D-Pro-D-Thr.

* * * * *